(12) United States Patent
Okaguchi

(10) Patent No.: US 10,124,096 B2
(45) Date of Patent: Nov. 13, 2018

(54) SUCTION DEVICE

(71) Applicant: Murata Manufacturing Co., Ltd., Kyoto (JP)

(72) Inventor: Kenjiro Okaguchi, Kyoto (JP)

(73) Assignee: MURATA MANUFACTURING CO., LTD., Kyoto (JP)

(*) Notice: Subject to any disclaimer, the term of this patent is extended or adjusted under 35 U.S.C. 154(b) by 0 days.

(21) Appl. No.: 15/402,792

(22) Filed: Jan. 10, 2017

(65) Prior Publication Data

US 2017/0143879 A1    May 25, 2017

Related U.S. Application Data

(63) Continuation of application No. PCT/JP2015/068749, filed on Jun. 30, 2015.

(30) Foreign Application Priority Data

Jul. 11, 2014 (JP) ................. 2014-143120

(51) Int. Cl.
*A61M 1/00* (2006.01)
*A61M 1/06* (2006.01)
(Continued)

(52) U.S. Cl.
CPC ........ *A61M 1/0031* (2013.01); *A61M 1/0066* (2013.01); *A61M 1/06* (2013.01);
(Continued)

(58) Field of Classification Search
CPC ............. F04B 45/047; F04B 49/065; F04B 2203/0201; F04B 2203/0202; F04B 37/10;
(Continued)

(56) References Cited

U.S. PATENT DOCUMENTS 4,344,743 A * 8/1982 Bessman ............ F04B 49/06
310/324
4,468,581 A * 8/1984 Okada ............... H03L 7/02
310/316.01
(Continued)

FOREIGN PATENT DOCUMENTS

JP        2618685 B2    6/1997
JP      H10-026550 A    1/1998
(Continued)

OTHER PUBLICATIONS

International Search Report issued in Application No. PCT/JP2015/068749 dated Oct. 6, 2015.
(Continued)

*Primary Examiner* — Kenneth J Hansen
*Assistant Examiner* — Benjamin Doyle
(74) *Attorney, Agent, or Firm* — Pearne & Gordon LLP

(57) ABSTRACT

A suction device (10) includes: a suction portion (11) that sucks an external fluid; a piezoelectric pump (21) that includes a piezoelectric element (22) vibrating when a drive voltage is applied thereto and sucks the fluid via the suction portion (11) by vibration of the piezoelectric element (22); a detection circuit (32) that detects a phase difference between a current flowing through the piezoelectric element (22) and the drive voltage for the piezoelectric element; and a control unit (33) that performs a process on the basis of the phase difference detected by the detection circuit (32).

11 Claims, 7 Drawing Sheets

(51) Int. Cl.
    *F04B 43/06* (2006.01)
    *F04B 49/06* (2006.01)
    *F04B 45/047* (2006.01)

(52) U.S. Cl.
    CPC ..... *A61M 1/064* (2014.02); *A61M 2205/3327* (2013.01); *A61M 2205/3344* (2013.01); *A61M 2205/52* (2013.01); *A61M 2210/0618* (2013.01); *A61M 2210/1007* (2013.01); *F04B 43/06* (2013.01); *F04B 45/047* (2013.01); *F04B 49/065* (2013.01); *F04B 2203/0201* (2013.01)

(58) Field of Classification Search
    CPC .............. A61M 1/0031; A61M 1/0644; A61M 1/0066; A61M 1/06; A61M 2205/3327; A61M 2205/3344; A61M 2205/52; A61M 2210/0618; A61M 2210/1007
    See application file for complete search history.

(56) References Cited

U.S. PATENT DOCUMENTS

| | | | | |
|---|---|---|---|---|
| 4,939,402 A * | 7/1990 | Hirayama | ............. | B06B 1/0261 310/316.01 |
| 5,113,116 A * | 5/1992 | Wilson | ................... | B06B 1/0253 310/316.01 |
| 6,074,178 A * | 6/2000 | Bishop | ................... | F04B 17/003 310/328 |
| 6,471,679 B1 | 10/2002 | Suh | | |
| 6,547,756 B1 * | 4/2003 | Greter | ............... | A61M 1/06 604/346 |
| 7,059,836 B2 * | 6/2006 | Takagi | ............... | F04B 39/1093 417/413.2 |
| 7,942,650 B2 * | 5/2011 | Kitahara | ............... | F04B 43/046 138/30 |
| 8,080,702 B2 * | 12/2011 | Blott | ................... | A61F 13/0213 602/41 |
| 9,033,683 B2 * | 5/2015 | Kodama | ............... | A61B 5/0235 137/510 |
| 9,433,359 B2 * | 9/2016 | Sano | ................... | F04B 43/046 |
| 9,711,706 B2 * | 7/2017 | Okaguchi | ............... | H01L 41/042 |
| 2002/0114716 A1 * | 8/2002 | Takagi | ................... | F04B 11/0008 417/413.2 |
| 2002/0164255 A1 * | 11/2002 | Burr | ....................... | F04B 35/045 417/363 |
| 2003/0017063 A1 * | 1/2003 | Komatsu | ............... | F04B 43/046 417/413.2 |
| 2004/0013539 A1 * | 1/2004 | Takagi | ............... | F04B 39/1093 417/300 |
| 2005/0052813 A1 * | 3/2005 | Kobayashi | ............... | G01G 3/16 361/143 |
| 2005/0234400 A1 * | 10/2005 | Onuki | ................... | A61M 1/06 604/74 |
| 2008/0177224 A1 * | 7/2008 | Kelly | ................... | A61M 1/0037 604/74 |
| 2009/0162224 A1 * | 6/2009 | Wakabayashi | ........ | F04B 17/003 417/410.2 |
| 2009/0232683 A1 * | 9/2009 | Hirata | ................... | F04B 43/046 417/413.2 |
| 2009/0232684 A1 * | 9/2009 | Hirata | ................... | F04B 39/1093 417/413.2 |
| 2009/0243431 A1 * | 10/2009 | Ohsawa | ............... | F04B 43/046 310/317 |
| 2010/0057269 A1 * | 3/2010 | Farmer | ................... | B03C 3/763 700/298 |
| 2011/0076170 A1 * | 3/2011 | Fujisaki | ................ | F04B 45/047 417/415 |
| 2012/0096942 A1 * | 4/2012 | Hayashi | ................... | G01C 19/56 73/504.12 |
| 2012/0116298 A1 * | 5/2012 | Van Schijndel | ...... | A61B 5/0533 604/74 |
| 2012/0171062 A1 * | 7/2012 | Kodama | ................ | F04B 43/046 417/413.2 |
| 2012/0277636 A1 * | 11/2012 | Blondheim | ............ | A61B 5/11 600/595 |
| 2013/0064683 A1 * | 3/2013 | Oshima | ................... | F04B 23/04 417/44.1 |
| 2013/0178752 A1 * | 7/2013 | Kodama | ............... | A61B 5/0235 600/498 |
| 2013/0323085 A1 * | 12/2013 | Hirata | ................... | F04B 43/043 417/44.2 |
| 2014/0148704 A1 * | 5/2014 | Ito | ........................... | A61B 1/127 600/462 |
| 2016/0038699 A1 * | 2/2016 | Higashiyama | ........ | A61M 39/24 128/207.15 |
| 2016/0201665 A1 * | 7/2016 | Hirata | ................... | F04B 41/06 417/278 |
| 2016/0271305 A1 * | 9/2016 | Kurihara | ............... | A61M 1/0023 |
| 2017/0035951 A1 * | 2/2017 | Tanaka | ................... | A61M 1/06 |
| 2017/0112697 A1 * | 4/2017 | Tanaka | ................... | A61G 7/057 |
| 2017/0143878 A1 * | 5/2017 | Tanaka | ................... | A61M 1/0031 |
| 2017/0143879 A1 * | 5/2017 | Okaguchi | ............ | A61M 1/0031 |

FOREIGN PATENT DOCUMENTS

| | | |
|---|---|---|
| JP | 2001-218831 A | 8/2001 |
| JP | 2009-264135 A | 11/2009 |
| JP | 2013-027625 A | 2/2013 |
| JP | 2013-220321 A | 10/2013 |

OTHER PUBLICATIONS

Written Opinion issued in Application No. PCT/JP2015/068749 dated Oct. 6, 2015.

* cited by examiner

THICKNESS DIRECTION
LONGITUDINAL DIRECTION
WIDTHWISE DIRECTION

SUCTION DEVICE

This is a continuation of International Application No. PCT/JP2015/068749 filed on Jun. 30, 2015 which claims priority from Japanese Patent Application No. 2014-143120 filed on Jul. 7, 2014. The contents of these applications are incorporated herein by reference in their entireties.

BACKGROUND OF THE DISCLOSURE

Field of the Disclosure

The present disclosure relates to a suction device used in sucking a fluid such as snivel, sputum, breast milk, or the like.

Description of the Related Art

In recent years, an electric inhalator (suction device) has been popularized which is able to suck snivel, sputum, breast milk, or the like. Normally, the suction device is configured to include: a suction portion that sucks an external fluid; a suction pump that sucks the fluid from the suction portion; and a container that stores the sucked fluid therein (see, e.g., Patent Document 1).

Patent Document 1: Japanese Unexamined Patent Application Publication No. 2001-218831

BRIEF SUMMARY OF THE DISCLOSURE

In the existing suction device, a motor is generally used as a power source for the suction pump. However, for the purpose of sucking a body fluid such as snivel, sputum, breast milk, or the like, there is a high demand for the reduction in noise or size of a suction device, and thus the inventor of the present application has proceeded with the development of a suction device in which a piezoelectric element is used as a power source for a suction pump.

Hereinafter, the contents considered by the inventor of the present application will be described.

In a suction device in which a piezoelectric element is used, the output of the piezoelectric element increases with the passage of time in some cases due to the self-heat generation occurring with the driving of the piezoelectric element. Thus, in the case where the suction pressure by the suction device is set relatively high, an excessive suction state occurs in which the suction pressure exceeds −20 kPa which is considered suitable for the suction from the oral cavity or the nasal cavities, so that there is a possibility of damaging the skin or mucosa of a target part with which the suction portion is brought into contact.

In addition, when the suction portion of the suction device and the target part are not sufficiently in close contact with each other, a non-sucked state occurs in which fluid in the target part cannot be sufficiently sucked. Thus, the present inventors consider that it is preferable to confirm the suction device is in a non-sucked state.

From these, the suction device preferably has a function to detect the suction pressure for grasping an excessive suction state or a non-sucked state. To make the suction device have a function to detect the suction pressure, a pressure sensor may be provided. However, the introduction of the pressure sensor makes the configuration of the suction device complicated. In addition, it may also be possible to estimate the state of the suction pressure from the current consumption of the suction pump. However, when the suction pressure of the suction pump is estimated from the current consumption, it is not possible to accurately estimate the suction pressure only under the predetermined condition such as a drive voltage (voltage amplitude) for the suction pump being constant.

Therefore, an object of the present disclosure is to provide a suction device that is able to perform a process corresponding to a suction pressure with high accuracy without using a pressure sensor.

A suction device according to the present disclosure includes a suction portion having a sidewall with at least one opening, a piezoelectric pump, a detection unit, and a control unit. The suction portion is configured to suck an external fluid. The piezoelectric pump includes a piezoelectric element configured to vibrate when a drive voltage is applied thereto, and is configured to suck the fluid via the suction portion by vibrating the piezoelectric element. The detection unit is configured to detect a phase difference between a current flowing through the piezoelectric element and the drive voltage for the piezoelectric element. The control unit is configured to perform a process on the basis of the phase difference detected by the detection unit.

In this configuration, the phase difference (hereinafter, referred to as current-voltage phase difference) between the current flowing through the piezoelectric element (current consumption) and the drive voltage for the piezoelectric element corresponds to the suction pressure of the piezoelectric pump. Thus, by being based on the current-voltage phase difference, even under a condition in which the drive voltage varies or the temperature varies, it is possible to perform a process corresponding to the suction pressure of the piezoelectric pump, with high accuracy. In addition, the current-voltage phase difference is less likely to be influenced by temperature change, and due to this as well, it is possible to perform a process corresponding to the suction pressure, with high accuracy. In this configuration, it is not necessary to additionally provide a pressure sensor as a detection unit, so that it is possible to simplify the configuration of the suction device. Furthermore, in the piezoelectric element, it is possible to make the frequency of the drive voltage outside of the frequency of audible sound to reduce the operating sound as compared to a power source such as a motor.

Preferably, the suction device further includes a storage unit having previously stored a correspondence relationship between: the phase difference between the current flowing through the piezoelectric element and the drive voltage for the piezoelectric element; and a suction pressure of the piezoelectric pump, and the control unit performs the process on the basis of the phase difference detected by the detection unit, by referring to the storage unit.

Preferably, the control unit stops the application of the drive voltage to the piezoelectric pump when the suction pressure of the piezoelectric pump exceeds a first threshold. In this configuration, it is possible to prevent the output of the piezoelectric element from increasing with the passage of time, due to the self-heat generation or the like occurring with the driving of the piezoelectric element, to cause an excessive suction state to damage the skin or mucosa of a target part with which the suction portion is brought into contact with.

Preferably, the control unit starts the application of the drive voltage to the piezoelectric pump when the predetermined time elapses after the suction pressure of the piezoelectric pump exceeds the first threshold and the application of the drive voltage to the piezoelectric pump is stopped. In this configuration, by detecting the suction pressure on the basis of the current-voltage phase difference of the piezoelectric pump, it is possible to prevent an excessive suction state from occurring.

Preferably, the suction device further includes an informing unit configured to inform information, and the control unit causes the informing unit to inform information regarding the suction pressure of the piezoelectric pump. In this configuration, it is possible to inform a user of information regarding the suction pressure of the piezoelectric pump via the informing unit. A liquid crystal display unit, a display lamp, a buzzer, a wireless communication unit, or the like may be used as the informing unit.

Preferably, when the suction pressure of the piezoelectric pump is smaller than a second threshold, the control unit causes the informing unit to inform information indicating it is in a non-sucked state. In this configuration, a user is allowed to confirm that it is in a non-sucked state.

Preferably, when a state where the suction pressure of the piezoelectric pump is smaller than the second threshold continues for a time longer than a threshold time, the control unit stops the application of the drive voltage to the piezoelectric pump. In this configuration, it is possible to stop driving of the piezoelectric pump to reduce power consumption, when it is in a non-sucked state.

Preferably, when the suction pressure of the piezoelectric pump exceeds −20 kPa, the control unit stops the application of the drive voltage to the piezoelectric pump. In this case, the suction portion preferably has such a shape as to be inserted into the nasal cavity. Thus, it is possible to suck snivel while the skin or mucosa of the nasal cavity is prevented from being damaged. In addition, the suction portion preferably has a shape along a breast. Thus, it is possible to suck breast milk while the skin or mucosa of the breast is prevented from being damaged. Moreover, the suction portion preferably has such a shape as to be inserted into the throat part. Thus, it is possible to suck sputum while the skin or mucosa of the throat part is prevented from being damaged.

According to the present disclosure, it is possible to perform a process corresponding to a suction pressure, with high accuracy without using a pressure sensor, in the suction device.

Figure 3A:
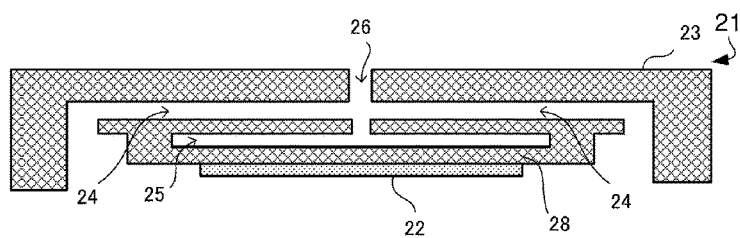
Figure 3B:
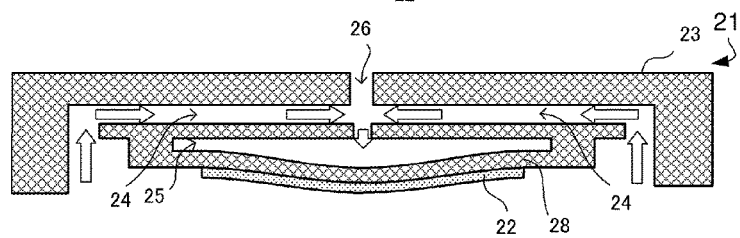
Figure 3C:
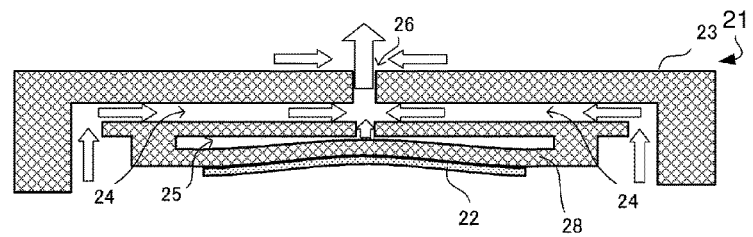

Each of FIGS. 3A, 3B and 3C is a schematic diagram showing a vibration mode of the suction pump according to the first embodiment.

Figure 4:
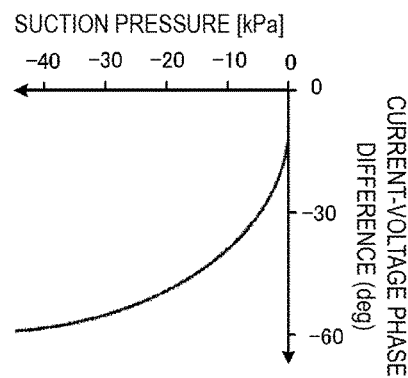

FIG. 4 is a graph showing a correspondence relationship between a current-voltage phase difference and a suction pressure.

Figure 5:
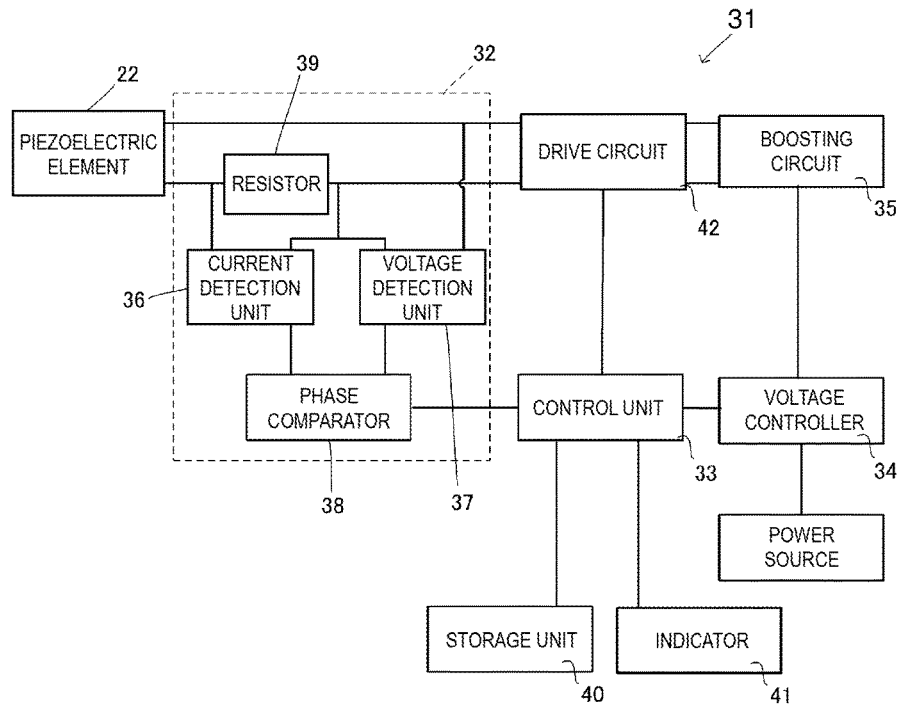

FIG. 5 is a block diagram of a drive control unit according to the first embodiment.

Figure 6:
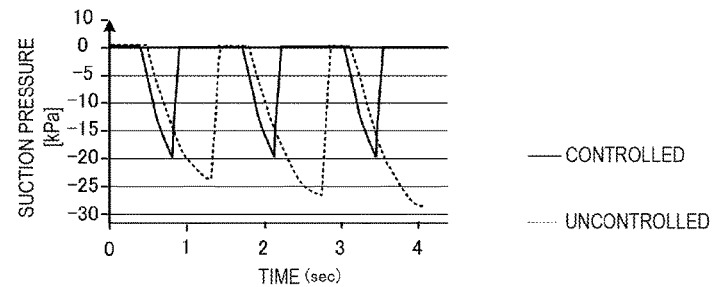

FIG. 6 is a graph showing a pattern of a suction pressure controlled by the drive control unit according to the first embodiment.

Figure 7:
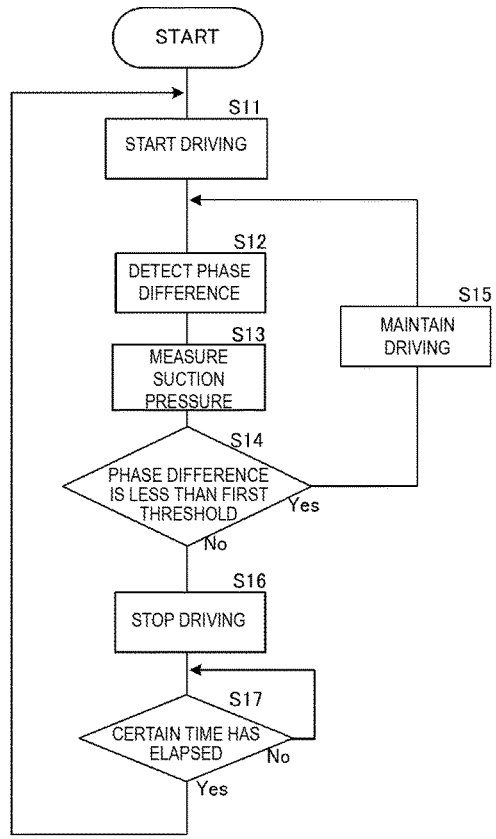

FIG. 7 is a flowchart showing a first operation example of the drive control unit according to the first embodiment.

Figure 8:
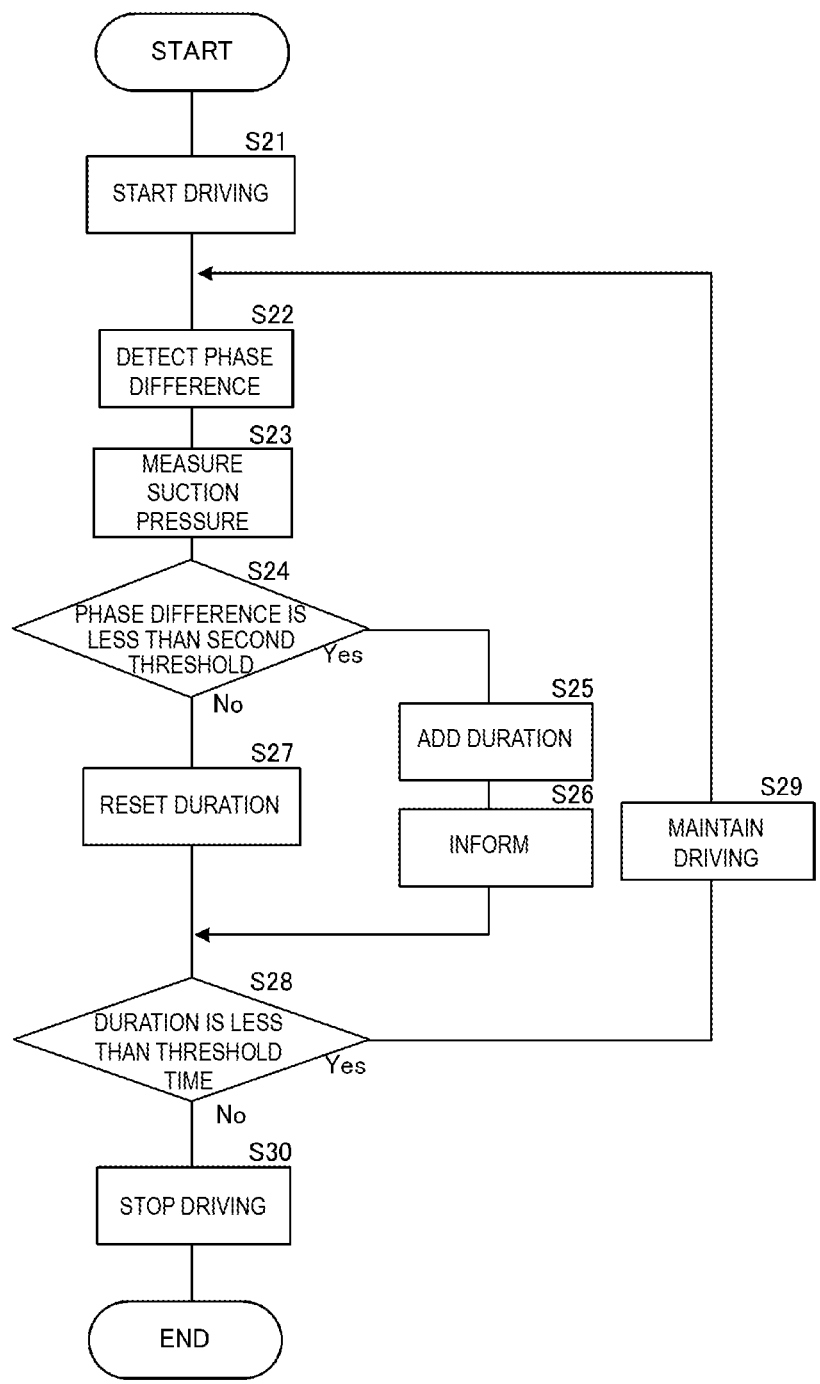

FIG. 8 is a flowchart showing a second operation example of the drive control unit according to the first embodiment.

Figure 9:
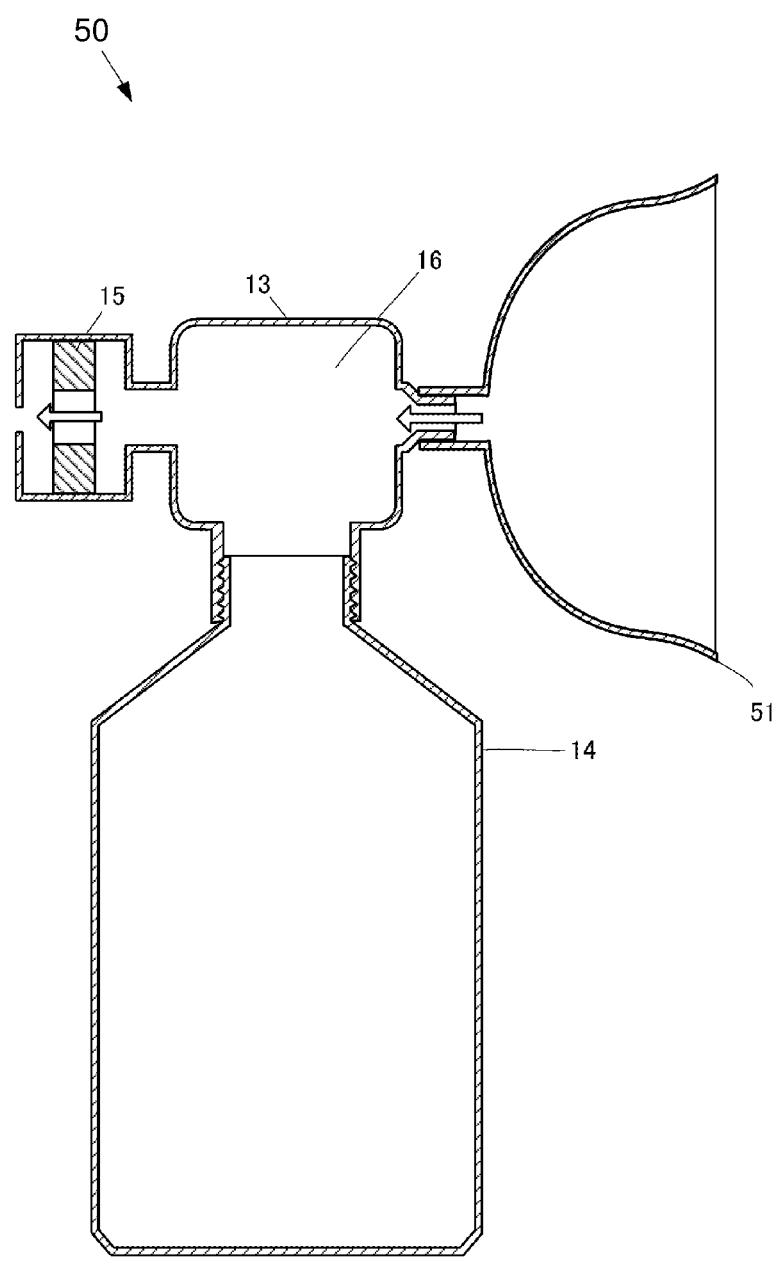

FIG. 9 is a schematic cross-sectional view of a suction device according to a second embodiment.

Figure 10:
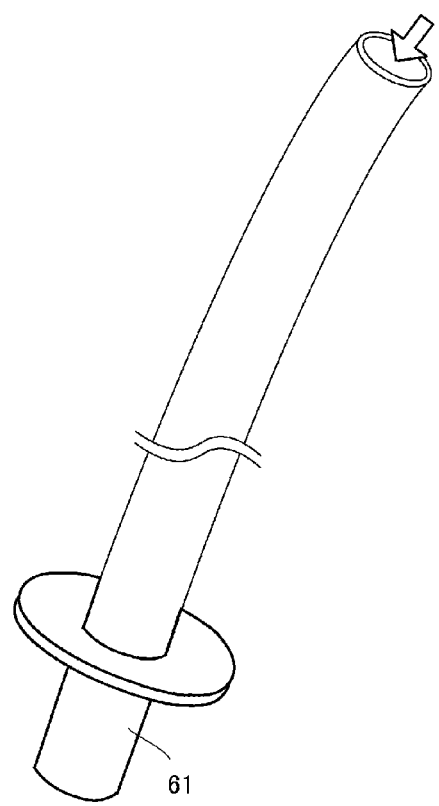

FIG. 10 is a perspective view showing a suction portion of a suction device according to a third embodiment.

DETAILED DESCRIPTION OF THE DISCLOSURE

<<First Embodiment>>

Hereinafter, a suction device 10 according to a first embodiment of the present disclosure will be described.

Figure 1:
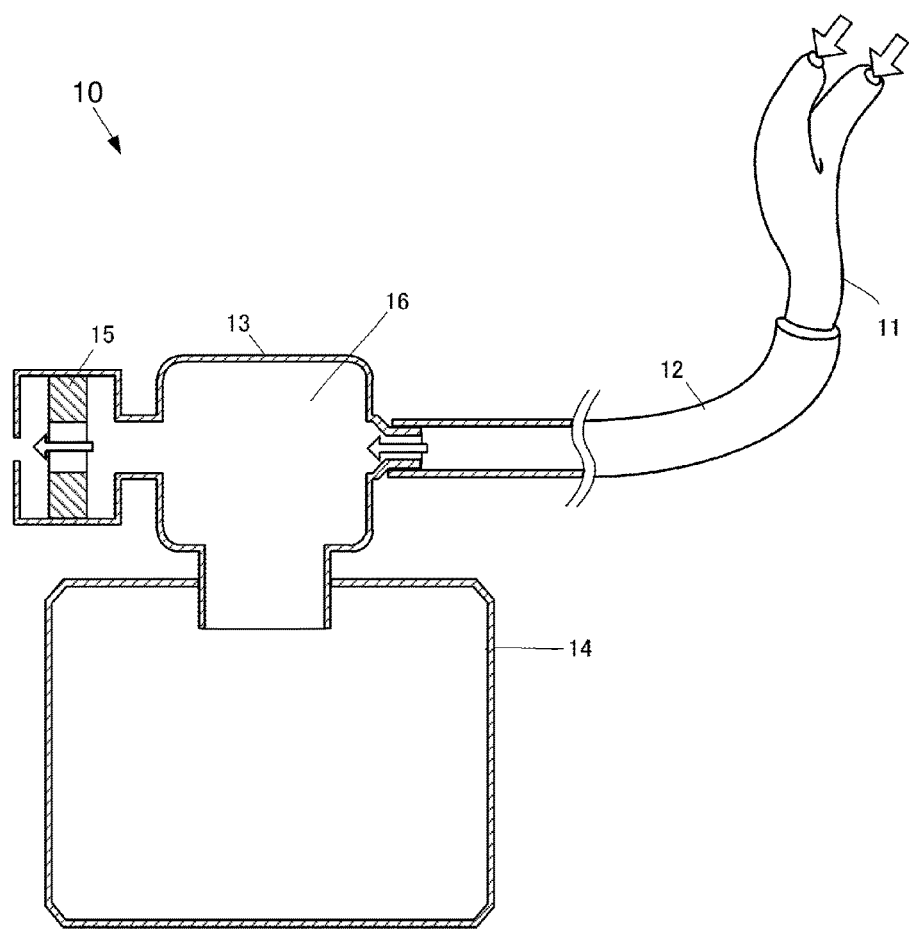
FIG. 1 is a schematic cross-sectional view of a suction device according to a first embodiment.

FIG. 1 is a schematic cross-sectional view of the suction device 10. The suction device 10 includes a suction portion 11, a separator 13, a container 14, and a piezoelectric drive portion 15. The suction device 10 is a snivel suction device, and the suction portion 11 is formed as a so-called nose piece having a shape that allows the suction portion 11 to simultaneously insert into the right and left nasal cavities. The separator 13 has a container shape that is open downward. The container 14 has a container shape that is open upward, and is provided below the separator 13. In addition, although not shown in FIG. 1, the suction device 10 is provided with an indicator 41 (see FIG. 4) that indicates a suction state at the suction portion 11. Moreover, the piezoelectric drive portion 15 is provided with a piezoelectric pump 21 (see FIG. 2) and a drive control unit 31 (see FIG. 4).

The suction portion 11, the separator 13, and the piezoelectric drive portion 15 are connected to each other in a state where the suction portion 11, the separator 13, and the piezoelectric drive portion 15 are arranged in this order from the front toward the rear of the suction device 10. A flow passage 16 is provided in the suction portion 11, the separator 13, the container 14, and the piezoelectric drive portion 15 so as to extend from the front end of the suction portion 11 to the rear end of the piezoelectric drive portion 15.

When the piezoelectric drive portion 15 is driven, flow of a fluid from the front end of the suction portion 11 toward the rear end of the piezoelectric drive portion 15 occurs in the flow passage 16. Accordingly, the suction portion 11 sucks snivel within the nasal cavities together with air. The separator 13 separates the snivel and the air sucked from the suction portion 11, and drops the separated snivel. The container 14 stores therein the snivel that drops from the separator 13.

Figure 2:
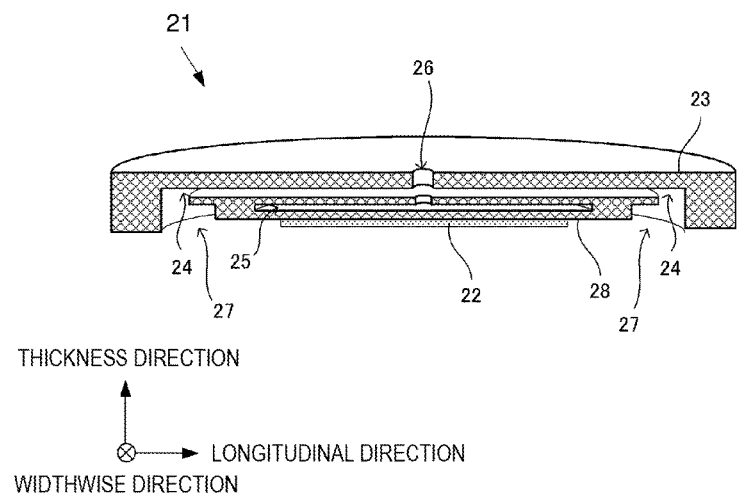
FIG. 2 is a cross-sectional view of a suction pump according to the first embodiment.

FIG. 2 is a cross-sectional view of the piezoelectric pump 21. The piezoelectric pump 21 includes a piezoelectric element 22 and a structure 23. The structure 23 has a plate shape in which a general outer shape is thin in the thickness direction. A discharge port 26 is opened in the vicinity of the center of the top surface of the structure 23. A suction port 27 is opened in the vicinity of the edge of the bottom surface of the structure 23. The piezoelectric pump 21 is disposed such that the suction port 27 side faces the separator 13 side.

Within the structure 23, a flow passage 24 and a pump chamber 25 are provided. The flow passage 24 leads to the discharge port 26 at the top surface of the structure 23, extends from the vicinity of the center to the outer peripheral side within the structure 23, and leads to the suction port 27 at the bottom surface of the structure 23. The pump chamber 25 is a thin cylindrical space provided at the bottom surface side of a communication portion between the discharge port 26 and the flow passage 24, and is opened to the communication portion between the discharge port 26 and the flow passage 24.

The inner bottom surface of the pump chamber 25 in the structure 23 is formed as a diaphragm (vibration plate) 28 capable of bending vibration. The diaphragm 28 has a disc shape and has a top surface that faces the pump chamber 25. The top surface of the diaphragm 28 opposes the discharge port 26 with the pump chamber 25 therebetween. The piezoelectric element 22 has a disc shape that is thin in the thickness direction, and is attached to the bottom surface of the diaphragm 28. The piezoelectric element 22 has piezoelectricity in which the piezoelectric element 22 attempts to stretch/contract in the in-plane direction of a principal surface thereof when an AC drive voltage is applied thereto.

Each of FIGS. 3A, 3B and 3C is a schematic diagram showing a vibration mode of the piezoelectric pump 21. The piezoelectric element 22 and the diaphragm 28 are attached to each other to form a unimorph structure, and are displaced in the thickness direction by driving of the piezoelectric element 22. Specifically, when the piezoelectric element 22 attempts to stretch from a stationary state shown in FIG. 3A, the diaphragm 28 convexly bends toward the piezoelectric element 22 side (bottom surface side) as shown in FIG. 3B, so that the volume of the pump chamber 25 increases. Accordingly, a negative pressure occurs in the pump chamber 25 and is transmitted to the flow passage 24, which communicates with the pump chamber 25, and the fluid in the flow passage 24 is sucked into the pump chamber 25.

When the piezoelectric element 22 attempts to contract from the stationary state shown in FIG. 3A, the diaphragm 28 convexly bends toward the pump chamber 25 side (top surface side) as shown in FIG. 3C, so that the volume of the pump chamber 25 decreases. Accordingly, since the pump chamber 25 and the discharge port 26 oppose each other with the flow passage 24 therebetween, the fluid in the pump chamber 25 is discharged through the discharge port 26 to the outside, and, by the flow of the fluid, the fluid within the flow passage 24 is drawn to be discharged through the discharge port 26.

With such bending vibration of the piezoelectric element 22 and the diaphragm 28, periodic volume change and pressure change repeatedly occur in the pump chamber 25 in the piezoelectric pump 21, so that an inertial force acts on flow of gas. Accordingly, flow of gas steadily occurs by which the fluid in the flow passage 24 is discharged through the discharge port 26. In the piezoelectric pump 21, since the diaphragm 28 opposes the discharge port 26 with the flow passage 24 and the pump chamber 25 therebetween, the fluid efficiency of the piezoelectric pump 21 is high, so that it is possible to achieve a high suction pressure and low power consumption at the same time.

The piezoelectric pump 21 is driven under control of the drive control unit 31 (see FIG. 5). The drive control unit 31 has a function to detect a suction pressure on the basis of a current-voltage phase difference at the piezoelectric element 22 and a function to control a pattern of a drive voltage for the piezoelectric element 22 on the basis of the detected suction pressure.

FIG. 4 is a graph showing a correspondence relationship between the current-voltage phase difference at the piezoelectric element 22 and the suction pressure. From the graph, it is possible to read that the current-voltage phase difference at the piezoelectric element 22 and the suction pressure have a one-to-one correspondence relationship. Specifically, it is possible to read that the current-voltage phase difference at the piezoelectric element 22 changes like a second-order curve relative to change of the suction pressure, that the higher the suction pressure (the absolute value) is, the greater the current-voltage phase difference (absolute value) is, and that the lower the suction pressure (the absolute value) is, the smaller the current-voltage phase difference (absolute value) is. As described above, the current-voltage phase difference at the piezoelectric element 22 changes in response to the suction pressure. Therefore, when the correspondence relationship between the current-voltage phase difference at the piezoelectric element 22 and the suction pressure is known, it is possible to grasp the suction pressure by detecting the drive voltage and the current actually flowing through the piezoelectric element 22 and measuring the current-voltage phase difference.

FIG. 5 is a block diagram showing a configuration example of the drive control unit 31. The drive control unit 31 includes a detection circuit 32, a control unit 33, a storage unit 40, a voltage controller 34, a boosting circuit 35, a drive circuit 42, and the indicator 41.

The voltage controller 34 controls a power source voltage, and supplies the power source voltage to the boosting circuit 35. The boosting circuit 35 boosts the power source voltage, and the drive circuit 42 generates a drive voltage having a frequency commanded by the control unit 33 and corresponding to the output of the boosting circuit 35, and applies the drive voltage to the piezoelectric element 22. Accordingly, the piezoelectric element 22 is driven to suck an external fluid into the suction portion 11.

The frequency of the drive voltage for the piezoelectric element 22 is outside of the frequency band of audible sound, and thus driving sound of the piezoelectric element 22 is quieter than that of a motor or the like. In addition, the piezoelectric element 22 has a property that the current-voltage phase difference is influenced in accordance with the pressure of the fluid (suction pressure) flowing through the flow passage 24 shown in FIG. 2.

The detection circuit 32 corresponds to a detection unit of the present disclosure and includes a current detection unit 36, a voltage detection unit 37, a phase comparator 38, and a resistor 39. The current detection unit 36 detects the current flowing through the piezoelectric element 22, from a voltage between both ends of the resistor 39 whose resistance value is known. The resistor 39 is inserted to a voltage line connecting the piezoelectric element 22 and the drive circuit 42. The voltage detection unit 37 detects the drive voltage applied to the piezoelectric element 22. The phase comparator 38 outputs an output signal corresponding to the phase difference (current-voltage phase difference) between the current detected by the current detection unit 36 and the voltage detected by the voltage detection unit 37.

The storage unit 40 previously stores therein the correspondence relationship between the current-voltage phase difference at the piezoelectric element 22 and the suction pressure, as a table or a calculation formula. The control unit 33 refers to the output of the phase comparator 38 at the storage unit 40 and grasps the suction pressure corresponding to the current-voltage phase difference of the piezoelectric element 22. Then, the control unit 33 sets the voltage controller 34 on the basis of this suction pressure. The voltage controller 34 controls the drive voltage outputted from the boosting circuit 35, by controlling a boosting ratio of the boosting circuit 35. The indicator 41 has a function to display information about the suction pressure grasped by the control unit 33, on a liquid crystal display portion, a display lamp, or the like, and a function to send the information via a communication line to the outside.

For example, a circuit-system digital comparator such as a phase frequency comparator used in a PLL (Phase Locked Loop) or the like may be used as the phase comparator 38. In addition, the control unit 33 and the voltage controller 34 may be configured, for example, in a microcomputer. In the case of using a microcomputer that performs PWM control, an I/O terminal of the microcomputer is connected to the detection circuit 32, and a PWM output terminal of the microcomputer is directly connected to the boosting circuit

35. The microcomputer is able to control the voltage outputted from the boosting circuit 35, by changing a duty ratio of PWM control output.

By configuring the drive control unit 31 as described above, it is made possible to detect the suction pressure with high accuracy by the detection circuit 32 and the control unit 33 even under a condition in which the drive voltage varies or the temperature changes. Therefore, it is not necessary to provide a pressure sensor that directly detects the suction pressure, so that it is possible to prevent the configuration of the suction device 10 from being complicated.

Next, examples of controlling the drive voltage and the suction pressure on the basis of the current-voltage phase difference will be described. First, a first control example will be described in which output of the piezoelectric element increases due to the self-heat generation occurring with driving of the piezoelectric element 22, to cause an excessive suction state.

FIG. 6 is a graph showing a temporal change of the suction pressure according to the first control example. A solid line shown in FIG. 6 corresponds to the temporal change of the suction pressure in the case where the drive voltage is controlled to be outputted intermittently with a fixed amplitude, and an output time and a pause time of the drive voltage are controlled on the basis of the current-voltage phase difference. A broken line shown in FIG. 6 corresponds to the temporal change of the suction pressure for comparison, and shows the case where the drive voltage is controlled to be outputted with a fixed suction pressure at a fixed period.

In the case of the comparative example shown by the broken line in FIG. 6, each of the application time and the pause time of the drive voltage to the piezoelectric element 22 is set as a fixed time interval such that the suction pressure has an assumed magnitude (−20 kPa that is considered suitable for the suction from the oral cavity or the nasal cavities), without grasping the magnitude of the actual suction pressure. Thus, in the comparative example, due to the self-heat generation occurring with driving of the piezoelectric element 22, temperature rise occurs in the piezoelectric element 22, and the output of the piezoelectric element 22 increases with the passage of time. Accordingly, in some cases, the actual suction pressure becomes higher than as assumed initially and exceeds −20 kPa, which is considered suitable for the suction from the oral cavity or the nasal cavities. When an excessive suction state where the suction pressure exceeds −20 kPa occurs, the skin or mucosa of the nasal cavities with which the suction portion 11 is brought into contact may be damaged.

On the other hand, in the case of the first control example shown by the solid line in FIG. 6, since it is possible to grasp the magnitude of the actual suction pressure on the basis of the current-voltage phase difference, the drive voltage is continuously applied to the piezoelectric element 22 until the suction pressure becomes about −20 kPa, and the application of the drive voltage to the piezoelectric element 22 is stopped when the suction pressure reaches about −20 kPa. By detecting the actual suction pressure and controlling the patterns of the drive voltage and the suction pressure as described above, it is made possible to prevent the suction device 10 from coming into an excessive suction state.

FIG. 7 is a flowchart showing the operation flow of the drive control unit 31 according to the first control example.

First, the drive control unit 31 starts the application of a drive voltage that is set at the predetermined amplitude, to the piezoelectric element 22 (S11). Accordingly, the piezoelectric element 22 is driven, and the suction device 10 starts the snivel suction operation via the suction portion 11. Next, the drive control unit 31 detects the current-voltage phase difference (S12). Then, the drive control unit 31 measures the magnitude of the actual suction pressure on the basis of the detected phase difference (S13).

Next, the drive control unit 31 compares the measured suction pressure to a previously registered first threshold (−20 kPa) (S14). Then, when the measured suction pressure is less than the first threshold (S14: Yes), the drive control unit 31 continues the application of the drive voltage to maintain the driving (S15), and returns to the current-voltage phase difference detecting step again (S12). On the other hand, when the measured suction pressure exceeds the first threshold (S14: No), the drive control unit 31 stops the application of the drive voltage (S16). Then, the drive control unit 31 waits for elapse of the predetermined time (S17) and returns again to the step of starting application of the drive voltage (S11).

By the operation flow of the first control example described above, it is possible to set the patterns of the drive voltage and the suction pressure as shown by the solid line in FIG. 6 described above, so that it is possible to prevent the suction device 10 from coming into an excessive suction state.

Next, a second control example will be described in which, when a non-sucked state where snivel within the nasal cavities cannot be sucked by the suction portion 11 continues for a long period of time, information regarding the non-sucked state is informed and control of the drive voltage and the suction pressure corresponding to the non-sucked state is performed.

FIG. 8 is a flowchart showing the operation flow of the drive control unit 31 according to the second control example.

First, the drive control unit 31 starts the application of a drive voltage that is set at the predetermined amplitude, to the piezoelectric element 22 (S21). Accordingly, the piezoelectric element 22 is driven, and the suction device 10 starts the snivel suction operation via the suction portion 11. Next, the drive control unit 31 detects the current-voltage phase difference (S22). Then, the drive control unit 31 measures the magnitude of the actual suction pressure on the basis of the detected phase difference (S23).

Next, the drive control unit 31 compares the measured suction pressure to a previously registered second threshold (−1 kPa) (S24). Then, when the measured suction pressure is less than the second threshold (S24: Yes), the drive control unit 31 performs a process of adding clocking of duration of a non-sucked state (S25). In addition, the drive control unit 31 performs an informing process of causing the indicator 41 to perform a display or sound emission indicating the non-sucked state (S26). On the other hand, when the measured suction pressure exceeds the second threshold (S24: No), the drive control unit 31 performs a process of resetting the clocking of duration of the non-sucked state (S27).

Next, the drive control unit 31 compares the clocked duration of the non-sucked state to a previously registered threshold time (e.g., 1 sec) (S28). Then, when the clocked duration of the non-sucked state is less than the threshold time (S28: Yes), the drive control unit 31 continues the application of the drive voltage to maintain the driving (S29), and returns again to the current-voltage phase difference detecting step (S22). On the other hand, when the clocked duration of the non-sucked state exceeds the threshold time (S28: No), the drive control unit 31 stops the application of the drive voltage (S29) and ends all the processes.

By the operation flow of the second control example described above, the user is allowed to confirm that the suction portion 11 is in a non-sucked state, by recognizing information about the non-sucked state by the indicator 41. In addition, when the non-sucked state continues beyond the threshold time, the application of the drive voltage to the piezoelectric element 22 is stopped. Thus, it is possible to reduce the power consumption of the piezoelectric element 22, so that it is possible to extend the battery life.

The case where the current-voltage phase difference decreases when the actual suction pressure is low, and the current-voltage phase difference increases when the actual suction pressure is high, has been described above. However, depending on the configuration of the piezoelectric pump 21 or the configuration of the drive control unit 31, reversely, the current-voltage phase difference may increase when the actual suction pressure is low, and the current-voltage phase difference may decrease when the actual suction pressure is low. Thus, in each operation flow described above, the process in the step of measuring the suction pressure on the basis of the current-voltage phase difference is preferably changed as appropriate on the basis of the actual correspondence relationship between the current-voltage phase difference and the suction pressure.

In addition, the case where the control unit 33 detects the actual suction pressure and performs a process on the basis of the suction pressure has been described above. However, even when the control unit 33 does not detect the actual suction pressure, it is also possible to perform a process based on the suction pressure by using the current-voltage phase difference without any change.

<<Second Embodiment>>

Next, a suction device 50 according to a second embodiment of the present disclosure will be described.

FIG. 9 is a schematic cross-sectional view of the suction device 50. The suction device 50 includes a suction portion 51, a separator 13, a container 14, and a piezoelectric drive portion 15. The suction device 50 is a breast pump, and the suction portion 51 is configured as a breast milk pumping cup having a shape with a concave surface along a breast. The other configuration is almost the same as the configuration according to the first embodiment. Even in the case where the suction device 50 is configured as described above, it is preferable to detect the current-voltage phase difference of the piezoelectric element 22 and control the patterns of the drive voltage for the piezoelectric element 22 and the suction pressure such that the suction pressure of the piezoelectric pump 21 does not exceed −20 kPa. Accordingly, it is possible to prevent the piezoelectric pump 21 from coming into an excessive suction state, so that it is possible to suck breast milk while the skin or mucosa of a breast with which the suction portion 51 is brought into contact is prevented from being damaged.

<<Third Embodiment>>

Next, a suction device according to a third embodiment of the present disclosure will be described.

FIG. 9 is a perspective view of a suction portion 61 of a suction device 60 (not shown) according to the third embodiment of the present disclosure. The suction device 60 (not shown) is a sputum suction device, and the suction portion 61 is configured as a so-called catheter having a tubular shape such that the suction portion 61 is able to be inserted into the throat part via the nasal cavity. The other configuration is almost the same as the configuration according to the first embodiment. Even in the case where the suction device 60 (not shown) is configured as described above, it is preferable to detect the current-voltage phase difference of the piezoelectric element 22 and control the patterns of the drive voltage for the piezoelectric element 22 and the suction pressure such that the suction pressure of the piezoelectric pump 21 does not exceed −20 kPa. Accordingly, it is possible to prevent the piezoelectric pump 21 from coming into an excessive suction state, so that it is possible to suck sputum from the throat part while the skin or mucosa of the throat part or the nasal cavity with which the suction portion 61 is brought into contact is prevented from being damaged.

10, 50, 60 suction device
11, 51, 61 suction portion
13 separator
14 container
15 piezoelectric drive portion
16 flow passage
21 piezoelectric pump
22 piezoelectric element
23 structure
24 flow passage
25 pump chamber
26 discharge port
27 suction port
28 diaphragm
31 drive control unit
32 detection unit
33 control unit
34 voltage controller
35 boosting circuit
36 current detection unit
37 voltage detection unit
38 phase comparator
39 resistor
40 storage unit
41 indicator
42 drive circuit

The invention claimed is:

1. A suction device comprising:
   a suction portion having a sidewall with at least one opening configured to suck an external fluid;
   a piezoelectric pump including a piezoelectric element configured to vibrate when a drive voltage is applied to the piezoelectric pump, the piezoelectric pump being configured to suck the external fluid via the suction portion by vibrating the piezoelectric element;
   a detection circuit configured to detect a phase difference between a current flowing through the piezoelectric element and the drive voltage for the piezoelectric element, the detection circuit comprising a current detection unit, a voltage detection unit, and a phase comparator that outputs a signal corresponding to the phase difference between the current detected by the current detection unit and the voltage detected by the voltage detection unit; and
   a controller configured to detect a suction pressure of the piezoelectric pump based on the phase difference detected by the detection circuit.

2. The suction device according to claim 1, further comprising a storage unit having a previously stored correspondence relationship between: the phase difference between the current flowing through the piezoelectric element and the drive voltage for the piezoelectric element; and the suction pressure of the piezoelectric pump, wherein
   the controller detects the suction pressure of the piezoelectric pump based on the phase difference detected by the detection circuit, by referring to the storage unit.

3. The suction device according to claim 2, wherein the controller stops the application of the drive voltage to the piezoelectric pump when the suction pressure of the piezoelectric pump exceeds a first threshold.

4. The suction device according to claim 3, wherein the controller starts the application of the drive voltage to the piezoelectric pump when a predetermined time elapses after the suction pressure of the piezoelectric pump exceeds the first threshold and the application of the drive voltage to the piezoelectric pump is stopped.

5. The suction device according to claim 2, further comprising an informing unit configured to provide information, wherein:
- the controller causes the informing unit to provide information regarding the suction pressure of the piezoelectric pump, and
- the informing unit comprises at least one of a liquid crystal display, a display lamp, a buzzer, and a wireless communication device.

6. The suction device according to claim 5, wherein when the suction pressure of the piezoelectric pump is smaller than a second threshold, the controller causes the informing unit to provide information indicating the piezoelectric pump is in a non-sucked state.

7. The suction device according to claim 6, wherein when a state where the suction pressure of the piezoelectric pump is smaller than the second threshold continues for a time longer than a threshold time, the controller stops the application of the drive voltage to the piezoelectric pump.

8. The suction device according to claim 2, wherein when the suction pressure of the piezoelectric pump exceeds −20 kPa, the controller stops the application of the drive voltage to the piezoelectric pump.

9. The suction device according to claim 8, wherein the suction portion has a tubular shape configured to be inserted into a nasal cavity.

10. The suction device according to claim 8, wherein the suction portion has a shape with a concave surface configured to fit along a breast.

11. The suction device according to claim 8, wherein the suction portion has a tubular shape configured to be inserted into a throat part.

* * * * *